(12) United States Patent
Schlossman et al.

(10) Patent No.: US 9,254,398 B2
(45) Date of Patent: Feb. 9, 2016

(54) SELF-DISPERSIBLE COATED METAL OXIDE POWDER, AND PROCESS FOR PRODUCTION AND USE

(75) Inventors: David Schlossman, South Plainfield, NJ (US); Yun Shao, South Plainfield, NJ (US); Carl Orr, South Plainfield, NJ (US)

(73) Assignee: KOBO PRODUCTS INC., South Plainfield, NJ (US)

( * ) Notice: Subject to any disclaimer, the term of this patent is extended or adjusted under 35 U.S.C. 154(b) by 519 days.

(21) Appl. No.: 13/202,092

(22) PCT Filed: Mar. 23, 2010

(86) PCT No.: PCT/US2010/028333
§ 371 (c)(1),
(2), (4) Date: Sep. 13, 2011

(87) PCT Pub. No.: WO2010/111279
PCT Pub. Date: Sep. 30, 2010

(65) Prior Publication Data
US 2012/0003287 A1  Jan. 5, 2012

Related U.S. Application Data

(60) Provisional application No. 61/162,387, filed on Mar. 23, 2009.

(51) Int. Cl.
| | |
|---|---|
| *C09C 1/36* | (2006.01) |
| *A61Q 1/12* | (2006.01) |
| *A61K 8/02* | (2006.01) |
| *A61K 8/29* | (2006.01) |
| *A61K 8/58* | (2006.01) |
| *A61K 8/85* | (2006.01) |
| *B82Y 30/00* | (2011.01) |
| *C09C 1/24* | (2006.01) |
| *C09C 1/34* | (2006.01) |
| *C09C 1/40* | (2006.01) |
| *C09C 3/06* | (2006.01) |
| *C09C 3/08* | (2006.01) |
| *C09C 3/12* | (2006.01) |
| *A61Q 17/04* | (2006.01) |
| *A61Q 19/00* | (2006.01) |

(52) U.S. Cl.
CPC ............... *A61Q 1/12* (2013.01); *A61K 8/0241* (2013.01); *A61K 8/29* (2013.01); *A61K 8/585* (2013.01); *A61K 8/85* (2013.01); *B82Y 30/00* (2013.01); *C09C 1/24* (2013.01); *C09C 1/346* (2013.01); *C09C 1/3661* (2013.01); *C09C 1/3669* (2013.01); *C09C 1/3684* (2013.01); *C09C 1/407* (2013.01); *C09C 3/063* (2013.01); *C09C 3/08* (2013.01); *C09C 3/12* (2013.01); *A61K 2800/28* (2013.01); *A61K 2800/412* (2013.01); *A61K 2800/621* (2013.01); *A61K 2800/622* (2013.01); *A61K 2800/63* (2013.01); *A61Q 17/04* (2013.01); *A61Q 19/00* (2013.01); *C01P 2004/62* (2013.01); *C01P 2004/64* (2013.01)

(58) Field of Classification Search
CPC ............ C09C 1/36; C09C 1/24; C09C 1/346; C09C 1/3661; C09C 1/3669; C09C 1/3684; C09C 1/407; C09C 3/063; C09C 3/08; C09C 3/12; A61K 8/0241; A61K 8/29; A61K 8/585; A61K 8/85; A61Q 1/12; A61Q 17/04; A61Q 19/00
See application file for complete search history.

(56) References Cited

U.S. PATENT DOCUMENTS

| | | | | |
|---|---|---|---|---|
| 4,927,464 | A * | 5/1990 | Cowie | 106/436 |
| 5,366,660 | A | 11/1994 | Tapley | |
| 5,560,917 | A * | 10/1996 | Cohen et al. | 424/401 |
| 5,730,893 | A | 3/1998 | Wyman et al. | |
| 2007/0065387 | A1 | 3/2007 | Beck et al. | |
| 2007/0089246 | A1 | 4/2007 | Brun | |

FOREIGN PATENT DOCUMENTS

WO   WO 2009126722 A1 * 10/2009 ............. A61Q 17/00

OTHER PUBLICATIONS

International Search Report dated May 19, 2010, issued in International Application No. PCT/US2010/028333.

* cited by examiner

*Primary Examiner* — Lezah Roberts
*Assistant Examiner* — Nannette Holloman
(74) *Attorney, Agent, or Firm* — Handal & Morofsky LLP

(57) ABSTRACT

Disclosed is a composition having a substrate comprising metal oxide particles. The substrate has a coating thereon that includes an organic dispersant present in a amount that renders the substrate self-dispersible. Also disclosed is a composition, such as a cosmetic composition, that includes that self-dispersible coated substrate, and a process that includes coating a particulate metal oxide with an organic dispersant to render the metal oxide self-dispersible.

22 Claims, No Drawings

SELF-DISPERSIBLE COATED METAL OXIDE POWDER, AND PROCESS FOR PRODUCTION AND USE

CROSS-REFERENCE TO RELATED APPLICATIONS

This application claims the benefit of U.S. Provisional Patent Application No. 61/162,387 filed Mar. 23, 2009.

BACKGROUND

The present application relates generally to a self-dispersible particle or powder, compositions containing the self-dispersible particle or powders, and methods for forming such particles or powders and compositions containing the particles or powders. Particularly useful compositions that may contain the self-dispersible particles or powders are cosmetic compositions.

Metal oxides such as titanium dioxide, zinc oxide, and iron oxides have been employed as attenuators of ultraviolet light in applications such as sunscreens, paints, coatings, and plastic films and resins. The metal oxide is often present in the end-product as dispersed particles, so better dispersion mechanisms are always needed.

Metal oxides of large or small particle size, even when coated like methicone and silane, are known to have poor dispersibility in esters, vegetable oil, mineral oil and hydrocarbons. Poor dispersibility can adversely affect UV attenuation and transparency in sunscreens and color strength in pigments, as well as skin feel and formulation stability.

Dispersion of micro metal oxides have been disclosed in literature. The process disclosed in the literature requires milling the metal oxides, and the milling process involves equipment that is not often available to many formulators. In many cases, only mechanical mixers or homogenizers are available to the formulator of the end-product to disperse particulates. Even when a milling process is available, the variation of formulation and complexity of ingredient will make the formulation of a proper dispersion difficult. In addition, cosmetic formulators are often not familiar with dispersion technology, and do not have time to find out the best dispersion and best use level for their system.

Therefore, there exists a need to improve the dispersibility of the pigment, for example metal oxides, so that the pigments give the desired performance even in the absence of the milling that requires extra machine and process.

SUMMARY

In one aspect, a self-dispersible metal oxide is disclosed that has a dispersing agent coated on the metal oxide that removes the need to separately add a dispersing agent and improves the dispersibility of the pigment. Disclosed herein is a particulate metal oxide having a coating that includes a polyhydroxy stearic acid in an amount that makes the particulate metal oxide self-dispersible. The particulate metal oxide may be titanium dioxide, zinc oxide, aluminum oxide, or an iron oxide.

In another aspect, a composition is disclosed that incorporates the self-dispersible particulate metal oxide into a dispersing medium to form a dispersion. The coated particulate metal oxide includes a particulate metal oxide substrate having a coating that includes a polyhydroxy stearic acid to modify the surface of the particulate metal oxide. The modified surface containing the polyhydroxy stearic acid provides the metal oxide with self-dispersing properties.

In another aspect, the coated particulate metal oxide is incorporated into a composition such as a cosmetic composition. The cosmetic composition may be liquid or dry make-up such as a sunscreen, foundation or pressed powder, lipstick, blush, eye-shadow, or mascara. Additionally, the cosmetic composition may be anhydrous or an emulsion.

Also disclosed herein is a process for rendering the particulate metal oxide self-dispersible. The process includes providing a particulate metal oxide substrate and coating the powder with a composition containing a polyhydroxy stearic acid.

DETAILED DESCRIPTION

The self-dispersible powder disclosed herein relates to a particulate metal oxide substrate coated an organic dispersant, a method for producing such coated metal oxides, and cosmetic formulations including the same.

The self-dispersible property of the coated metal oxide powder makes the powder especially attractive to formulators in the cosmetics industry enabling the novel coated powder to be specified for a wide range of applications without undue concern as to what dispersing agent and/or how much dispersing agent to use. Furthermore, the coated powder disclosed herein is suitable for a wide range of cosmetic compositions used in everyday cosmetic products. Unlimited examples include liquid or powder makeup, lipstick, nail enamel, eye shadow, and mascara Suitable metal oxides may include, without limitation, titanium dioxide, zinc oxide, iron oxide, alumina oxide, chromium oxide, composites of metal oxides or of a metal oxide and an inorganic salt, and combinations of these metal oxides. The metal oxides may have any desired regular or irregular shape including spherical or ball like particles (with regular or irregular porous surfaces), needles, rods, flakes, rhomboids, nodular, acicular, granular, ellipsoidal, hexagonal, prismatic, star-like, Y-shaped, and the like.

There is no particular limitation as to the particle size of the particulate metal oxides employed in the present self-dispersible powder. The metal oxide may include micronized particles (i.e., nanoparticles) or pigmentary grade particles. It may be beneficial to use metal oxides that are free of oversize particles that may impart grittiness and are also free of overly fine particles whose presence may be undesirable in the processes of the invention described herein.

As used herein, the terms "nanoparticles" and "micronized particles" are interchangeable and include a material having 5% or more of the nanoparticles, in which the nanoparticles have a size less than about 100 nm.

As used herein, the term pigmentary grade particles are particles having a size greater than 100 nm.

The micronized metal oxide may have a primary particle size of about 5 nm to about 150 nm if the particles are spherical or granular. If the particles are acicular the primary particle size may be about 5 nm to about 50 nm by about 50 nm to 150 nm. Primary particle size may be analyzed using TEM.

Suitable organic dispersants may include, without limitation, substituted carboxylic acids, soap bases and polyhydroxy acids. Examples of typical dispersing agents are those based on ricinoleic acid, hydroxy stearic acid, hydrogenated castor oil fatty acid which contains in addition to 12-hydroxystearic acid small amounts of stearic acid and palmitic acid as taught in the '753 patent and U.S. Pat. No. 7,220,305.

In one embodiment, the organic dispersant is polyhydroxy stearic acid. Polyhydroxy stearic acid is a polyester which is obtainable for example by heating hydroxy stearic acid, e.g.

commercial 12-hydroxystearic acid, 9- or 10-hydroxystearic acid, at 160° C. to 200° C. in the presence of an inert organic diluent, such as toluene or xylene, and removing from the reaction mixture the water formed in the course of esterification.

The organic dispersant, such as a polyhydroxy stearic acid, is contained in a coating of the metal oxide particles. The coating may be a solution that contains the organic dispersant in one or more suitable solvents, i.e., those capable of dissolving the organic dispersant, applied to the metal oxide particles that is allowed to dry. If the organic dispersant is polyhydroxy stearic acid, unlimited representative examples of the solvent may be isopropyl alcohol, hexane, heptane, isoheptane, isooctane, and isononane. The solvent may alternately be any solvent that dissolves the organic dispersant, promotes even distribution of the polyhydroxy stearic acid over the surface of the substrate powders, and may readily evaporate, optionally upon heating, to facilitate drying.

In one embodiment, the organic dispersant is present on the metal oxide particles in an amount that renders the metal oxide self-dispersible in an organic medium. In another embodiment, the organic dispersant is PHSA and is present on a metal oxide to provide improved adhesion characteristics, which makes the pigments easier to wet and any agglomerates formed are easier to break in powder or in liquid. Agglomerates are undesirable in cosmetics because it is believed that they create cavities that can entrap excessive oil. The PHSA may be applied as a 1% PHSA composition.

Suitable organic liquid medium for dispersing the self-dispersible metal oxide powder may include, without limitation, esters, oils, hydrocarbons, alkyl modified silicon fluid. Unlimited examples, for esters include diisopropyl adipate, isopropyl myristate, and butyl stearate, for oils include vegetable oil and mineral oil, for hydrocarbons include isododecane, and for the alkyl modified silicon fluid include caprylyl methicone, such as Silsoft 034. One of ordinary skill in the art will appreciate that there are many other esters, oils, hydrocarbons, and alkyl modified silicon fluids that will make suitable dispersing medium beyond the few examples listed here.

Optional Additional Coatings

The particulate metal oxide may comprise substantially pure metal oxide, but in one embodiment the metal oxide particles may include an inorganic coating in addition to the coating containing the organic dispersant. For example, the metal oxide particles may be coated with oxides of other elements such as oxides of aluminium, zirconium or silicon, or mixtures thereof such as alumina and silica as disclosed in GB-2205088-A, the teaching of which is incorporated herein by reference. The preferred amount of inorganic coating is in the range from 2% to 25%, more preferably 4% to 20%, particularly 6% to 15%, and especially 8% to 12% by weight, calculated with respect to the weight of particulate metal oxide. The inorganic coating may be applied using techniques known in the art. A typical process comprises forming an aqueous dispersion of metal oxide particles in the presence of a soluble salt of the inorganic element whose oxide will form the coating. This dispersion is usually acidic or basic, depending upon the nature of the salt chosen, and precipitation of the inorganic oxide is achieved by adjusting the pH of the dispersion by the addition of acid or alkali, as appropriate.

The inorganic coating, if present, is preferably applied as a first layer to the surface of the metal oxide. In addition to the inorganic coating, the particulate metal oxide may include a hydrophobic coating applied to the inorganic coating. The hydrophobic coating agent may be, for example, a silicone, a silane, a metal soap, a titanate, an organic wax, and mixtures thereof. The hydrophobic coating may alternatively include a fatty acid, for example, a fatty acid containing 10 to 20 carbon atoms, such as lauric acid, stearic acid, isostearic acid, and salts of these fatty acids. The fatty acid may be isopropyl titanium trisostearate. With respect to the silicone, the hydrophobic coating may be a methicone, a dimethicone, their copolymers or mixtures thereof. The silicone may also be an organosilicon compound, for example dimethylpolysiloxanes having a backbone of repeating -Me2SiO— units ("Me" is methyl, $CH_3$), methyl hydrogen polysiloxanes having a backbone of repeating -MeHSiO— units and alkoxysilanes of formula $R_nOSiH_{(4-n)}$ where "R" is alkyl and "n" is the integer 1, 2 or 3. With respect to the silane, the hydrophobic coating agent may be an alkoxysilanes, for example, an alkyltriethoxy or an alkyltrimethoxy silanes available from OSI Specialities or PCR. The alkoxysilane may be a triethoxycaprylylsilane or a perfluoroalkylethyl triethoxysilane having a C3 to C12 alkyl group that is straight or branched. One such alkoxysilane is Dynasylan® OCTEO available from Degussa AG. With respect to the metal soap, the hydrophobic coating agent may be a metal myristate, metal stearate, a metal palmitate, a metal laurate or other fatty acid derivatives known to one of skill in the art. The metal, for example, may be magnesium or aluminum. With respect to the titanate, the hydrophobic coating agent may be an organotitanate as taught in U.S. Pat. No. 4,877,604 to Mitchell Schlossman ("Schlossman '604" hereinafter), the disclosure of which is herein incorporated by reference thereto. Schlossman '604 discloses isopropyl titanium triisostearate as one preferred coating agent. With respect to the organic wax, the hydrophobic coating agent may be a synthetic wax like polyethylene or a natural wax like carnauba wax.

Depending upon which hydrophobic coating agent is employed a suitable solvent is needed. A suitable aprotic solvent can be employed for the functionalized silane or other silicon compound. Also, if desired the silane, can be solubilized in a volatile organic solvent such as isopropyl alcohol, heptane, isoheptane, isooctane, isononane and petroleum distillates such as those available from Phillips Chemical under the trade names or trademarks Soltrol 130, Soltrol 150 and Soltrol 170. Another useful solvent for functionalized silicon compounds is an isopar solvent. Isopar solvents are a range of solvents each comprising a high-purity, fractionated partially neutralized mixture of isoparaffinic acids which are available in different grades such as isopar C, which comprises C7-C8 solvents, isopar E or isopar G. Water or other suitable solvent may be employed for the organotitanate as described in Schlossman '604.

The hydrophobic coatings may be applied using any conventional process. Typically, metal oxide particles are dispersed in water and heated to a temperature in the range of about 50° C. to about 80° C. A fatty acid, for example, is then deposited on the metal oxide particles by adding a salt of the fatty acid (e.g. sodium stearate) to the dispersion, followed by an acid. Alternatively, the metal oxide core particles can be mixed with a solution of the water-repellent material in an organic solvent, followed by evaporation of the solvent. Generally, the particles are treated with up to 25%, more preferably in the range from 3% to 20%, particularly 6% to 17%, and especially 10% to 15% by weight of organic material calculated with respect to the metal oxide core particles.

If the inorganic coating is not present, but the hydrophobic coating is, the hydrophobic coating is preferably applied to the particulate metal oxide as a first layer. The inorganic and organic coatings may be present in various amounts as taught in U.S. Pat. No. 7,220,305, which is incorporated herein by reference in its entirety.

Organic Dispersant Coating Process

The organic dispersant coating may be applied to the metal oxide particulate or powder using a variety of techniques, including those known to a person of ordinary skill in the art. The metal oxide can be treated with a suitable coating agent in a liquid medium, for example by mixing or spraying the coating agent with or on the powder. Another method may involve making a slurry of the metal oxide and the organic dispersant.

Subsequently, the coated powder may be dried by heating to remove the solvents, optionally under vacuum if the solvents are volatile solvents. The mixture may be heated at a temperature of about 30° C. to about 150° C. to remove the solvent and dry the powder. Other suitable times and temperatures will be known to those of skill in the art, having regard to the materials employed, or can be determined without undue experimentation.

After the coated metal oxide powder is dry, the powder may be milled or pulverized using, for example, a jet mill, hammer mill, or other suitable mill to a desired size.

The treated powder may then be dried by heating to remove the solvent and further heated for about 1 to about 10 hours at a temperature of about 30° C. to about 150° C. For any of the embodiments disclosed herein the process may also include milling the treated powder to remove any agglomerates or overly sized coated powders.

Preferably, the reactants and reaction conditions employed in treating the metal oxide with the organic dispersant are selected to provide covalent bonding to metal oxide, hydroxide, carbonate, silicate or other reactive moieties on the surfaces of the particulate. However, ionic, hydrogen or van der Waals bonding in addition to, or in the alternative, may also provide satisfactory bonding between the coating and the substrate powder particle. The coating agent may react, for example, with hydroxyl groups, oxide ions, available oxygen atoms or other suitable reactive groups normally present on the surface of the cosmetic powder being coated.

Dispersions

In another aspect, the self-dispersible metal oxide powder having the organic dispersant coating thereon may be added to a dispersing medium to form a slurry, or preferably a liquid dispersion, of the metal oxides. The dispersing medium may be any suitable aqueous or organic liquid medium, such as those discussed above. By liquid dispersion is meant a true dispersion, i.e., where the solid particles are stable to aggregation. The particles in the dispersion are relatively uniformly dispersed and resistant to settling out on standing, but if some settling out does occur, the particles can be easily redispersed by simple agitation.

In one embodiment, a C12-C15 alcohol benzoate is mixed in a laboratory mixer, for example, a Hockeyer Lab mixer, at about 800-1000 rpm and treated micro $TiO_2$ was added slowly with mixing. When all the $TiO_2$ powder is added, the mixing speed may be increased, for example, to 1500 rpm. A dispersion of $TiO_2$ in the C12-C15 alcohol benzoate is obtained. In one embodiment, 0.5 kg of the treated micro $TiO_2$ with a primary size of about 15×80 nm was dispersed in 1 kg of Finsolv TN, a C12-C15 alcohol benzoate, available from Finetex, Inc. with the laboratory mixer according to this procedure to obtain a 40% dispersion of micro $TiO_2$. This method is one example of a suitable way to make a metal oxide dispersion and is not meant to be limiting.

Compositions Incorporating the Self-Dispersible Powder

In another aspect, any of the coated powders and/or a dispersion of the coated powders described herein may be incorporated into a cosmetic composition. The cosmetic compositions may be anhydrous or an emulsion. Some examples of cosmetic compositions in which the powders may be employed include liquid or dry make-ups such as foundation or pressed powder, lipsticks, blushes, eye-shadow, and mascara. The coated metal oxides are beneficial in cosmetic compositions in that the powders are self-dispersible, with enhanced dispersibility in organic liquid media, such as esters, oils, and hydrocarbons, and alkyl modified silicone fluids while still allowing the beneficial properties of the metal oxides to be used in the compositions, such as attenuating UV light while being transparent to visible light and reduced skin whitening.

Alternatively, the particulate metal oxide may be incorporated in the form of a lotion or cream of a solid and/or semi-solid dispersion. Suitable solid or semi-solid dispersions may contain, for example, in the range from 50% to 90%, preferably 60% to 85% by weight of particulate metal oxide according to the present invention, together with any one or more of the organic liquid media disclosed herein.

The particulate metal oxide and dispersions of the present invention are useful as ingredients for preparing sunscreen compositions, especially in the form of emulsions. The emulsion may be an oil-in-water, water-in-oil, or a water-in-silicon emulsion. The dispersion may further contain conventional additives suitable for use in the intended application, such as conventional cosmetic ingredients used in sunscreens. Because the metal oxides attenuate ultraviolet light, a sunscreen composition may include other sunscreen agents, such as organic materials. Suitable organic sunscreens include, without limitation, p-methoxy cinnamic acid esters, salicylic acid esters, p-amino benzoic acid esters, non-sulphonated benzophenone derivatives, derivatives of dibenzoyl methane and esters of 2-cyanoacrylic acid. Specific examples of useful organic sunscreens include benzophenone-1, benzophenone-2, benzophenone-3, benzophenone-6, benzophenone-8, benzophenone-12, isopropyl dibenzoyl methane, butyl methoxy dibenzoyl methane, ethyl dihydroxypropyl PABA, glyceryl PABA, octyl dimethyl PABA, octyl methoxycinnamate, homosalate, octyl salicylate, octyl triazone, octocrylene, etocrylene, menthyl anthranilate, and 4-methylbenzylidene camphor. Many other products that may benefit from such a versatile coated powder are known to those skilled in the art. The coated powders, for example, may be incorporated into other industrial products where the particle material is customarily used and where hydrophobic and lipophobic properties are beneficial, for example, in paints, coatings, and plastics.

Example 1

A self-dispersible particulate metal oxide powder was prepared with the following coatings applied there to in the order listed in Table 1.

TABLE 1

|  | Substance |
| --- | --- |
| Particulate Metal Oxide | $TiO_2$ |
| Inner Coating | triethoxycaprylylsilane |
| Outer Coating | polyhydroxy stearic acid |

The coated metal oxide disclosed in Table 1 may be prepared as follows:

One-Step Method

Here 1 g of polyhydroxy stearic acid and 2 g of triethyoxysilane were dissolved in isopropyl alcohol. The resultant solution was mixed with 100 g of Titanium dioxide (Tipaque PF-671 available from Kobo Products). The mixture was heated to remove the solvent and further heated at 100° C. for three hours to dry the powder. The dry powder was then milled to remove any large lumps.

Alternately, the coated metal oxide disclosed in Table 1 may be prepared as follows:

Two-Step Method:

Here 2 g of triethyoxysilane were dissolved in isopropyl alcohol. The resultant solution was mixed with 100 g of Titanium dioxide (Tipaque PF-671 available from Kobo Products). The mixture was heated to remove the solvent and further heated at 100° C. for three hours to dry the powder. The dry powder was then milled to remove any large lumps. A lotion of 1 g of polyhydroxy stearic acid in 3 g of isopropyl alcohol was sprayed on the dry powder. The powder was heated at 100° C. for 1 h. The dry powder was then milled to remove any large lumps.

Example 2

A dispersion was made using the coated metal oxide powder of Example 1.

1 kg of Finsolv TN, a C12-C15 alcohol benzoate, was placed in a 1 gal pail and mixed under a Hockeyer Lab mixer. The mixing speed was about 800-1000 rpm. While mixing, 2.33 kg of the treated $TiO_2$ from Example 1 was added slowly into the Finsolv TN in the mixer. Once all the powder was added, the mixing speed was increased to 1500 rpm and mixing continued for 15 min. A fluid, 70% dispersion was obtained.

Any composition, including a dispersion, that includes the self-dispersible coated substrate of metal oxides disclosed herein may include at least one biocompatible excipient, such as, without limitation a buffer (neutralizer or pH adjusters), emulsifier, surfactant, diluent, adjuvant, preservative, and/or electrolyte.

Example 3

In accordance with the invention, it has also been discovered that metal oxides coated in accordance with the invention are useful in the manufacture of compact powders. In particular, a compact powder was prepared using the Formula A ingredients of Table 2.

TABLE 2

| Formula | A % wt |
|---|---|
| Part 1 | |
| GMS-11S2 Mica (And) Triethoxycaprylylsilane | 35 |
| Talc N-11S2 Talc (And) Triethoxycaprylylsilane | 51.2 |
| BTD-11S2 Titanium Dioxide (And) Triethoxycaprylylsilane | 7.5 |
| BYO-11S2 Iron Oxide (And) Triethoxycaprylylsilane (Yellow Iron Oxide) | 0.9 |
| BRO-11S2 Iron Oxide (And) Triethoxycaprylylsilane (Red Iron Oxide) | 0.3 |
| BBO-11S2 Iron Oxide (And) Triethoxycaprylylsilane (Black Iron Oxide) | 0.1 |
| Part 2 | |
| Carnation white mineral oil | 5 |
| | no glaze |

The ingredients of Part 1 were blended using a pulverizer until the color was fully developed. The mineral oil of Part 2 was then added with blending using the pulverizer until the resulting mixture was well blended. The mixture was then pressed with a conventional compact powder fabricating device at 250 psi. The metal oxide in Formula A has only a hydrophobic coating.

Example 4

A second compact powder using the Formula B ingredients was made in accordance with the formulation in shown in Table 3.

TABLE 3

| Formula | B % wt |
|---|---|
| Part 1 | |
| GMS-11S2 + 1% PSHA Mica (And) Triethoxycaprylylsilane + 1% PSHA | 35 |
| Talc N-11S2 + 1% PSHA Talc (And) Triethoxycaprylylsilane | 51.2 |
| BTD-11S2 + 1% PHSA Titanium Dioxide (And) Triethoxycaprylylsilane + 1% PHSA | 7.5 |
| BYO-11S2 Iron Oxide (And) Triethoxycaprylylsilane (Yellow Iron Oxide) | 0.9 |
| BRO-11S2 Iron Oxide (And) Triethoxycaprylylsilane (Red Iron Oxide) | 0.3 |
| BBO-11S2 Iron Oxide (And) Triethoxycaprylylsilane (Black Iron Oxide) | 0.1 |
| Part 2 | |
| Carnation white mineral oil | 5 |
| | no glaze |

The ingredients of Part 1 were blended using a pulverizer until the color was fully developed. The mineral oil of Part 2 was then added with blending using the pulverizer until the resulting mixture was well blended. The mixture was then pressed with a conventional compact powder fabricating device at 250 psi. The metal oxide in Formula A has only a hydrophobic coating.

In contrast to the metal oxide in the compact pigments of Formula A, the metal oxide pigments in the compact of Formula B have a polyhydroxy stearic acid (PHSA) deposit over the hydrophobic treatment.

The products manufactured using Formula A and Formula B of Examples 3 and 4, respectively, were then drop tested by being dropped 12 inches onto a hard surface. The results of that test are noted in Table 4:

TABLE 4

| Formula | A<br>Test: 1 \| 2 \| 3 | B<br>Test: 1 \| 2 \| 3 |
|---|---|---|
| Number of drops to break | 2 \| 1 \| 1 | 2 \| 2 \| 4 |
| Average number of drops to break | 1.33 | 2.67 |

As can be seen from Table 4, significant mechanical integrity was added to the system using the inventive coating method. More particularly, in three tests, Formula A had to be dropped twice to break in one case, but broke on a single drop in the other two tests. In contrast, Formula B had to be dropped four times in one case in order to break, and in the other two trials had to be dropped twice, showing that the inventive method substantially increased mechanical resistance to breakage.

The drop test results also indicate that the PHSA coating surprisingly improves the pressability of the power. This means that less liquid binder needs to be used and the spreading of the powder on skin feel is smoother and less greasy.

Example 5

Another compact or pressed powder Formulation is shown in Table 5.

TABLE 5

|  | Ingredient | % wt |
|---|---|---|
| Part 1 | Sericite w/treatment | 35 |
|  | Talc N w/treatment | 51.2 |
|  | TiO$_2$ w/with treatment | 7.5 |
|  | BYO-11S2 | 0.9 |
|  | BRO-11S2 | 0.3 |
|  | BBO-11S2 | 0.1 |
| Part 2 | Dimethicone (SF96-350) | 5.0 |

Procedure

The ingredients of Part 1 were blended using a pulverizer until the color was fully developed. The dimethicone of Part 2 was then added with blending using the pulverizer until the resulting mixture was well blended. The mixture was then pressed with a conventional compact powder fabricating device at 250 psi.

The "treatment" of the sericite with treatment, the Talc N with treatment, and the TiO$_2$ with treatment of Table 5 includes:

Treatment A: Isopropyl Titanium Triisostearate treatment,
Treatment B: Triethoxycaprylylsilane treatment,
or Treatment C: Polyhydroxy stearic acid and triethoxycaprylylsilane treatment.

The treatments are applied using the procedure of Example 1.

Three different compact powders were formed using the procedure of Example 5 where the first compact powder included Treatment A, the second compact powder included Treatment B, and the third compact powder included Treatment C on sericite, Talc N, and TiO$_2$. Drop tests were performed on the three powders. The results of the tests are noted in Table 6:

TABLE 6

|  | Powder 1 with Treatment A | | Powder 2 with Treatment B | | Powder 3 with Treatment C | |
|---|---|---|---|---|---|---|
| Blending (sec) | Weight (gr.) | Drops | Weight (gr.) | Drops | Weight (gr.) | Drops |
| 20 | 12.14 | 2 | 12.45 | 2 | 12.59 | 2 |
| 50 | 12.80 | 3 | 12.30 | 5 | 10.40 | 7 |
| 50 | 12.02 | 3 | 12.48 | 4 | 13.04 | 7 |
| 50 | 13.39 | 4 | 11.37 | 4 | 10.80 | 7 |
| 50 | 13.25 | 2 | 11.20 | 3 | 11.04 | 7 |
| 50 | 12.70 | 4 | 11.22 | 5 | 11.65 | 5 |
|  |  | 3.0 |  | 3.8 |  | 5.8 |

As can be seen from Table 6, significant mechanical integrity was added to the system using the inventive coating method. More particularly, powder 3 with components of the composition treated with triethoxycaprylysilane and polyhydroxy stearic acid had a higher average number of drops indicating the highest impact resistance of the three powders made and tested. The test results show that the inventive method substantially increased mechanical resistance to breakage.

While illustrative embodiments have been described above, it is, of course, understood that various modifications will be apparent to those of ordinary skill in the art. Many such modifications are contemplated as being within the spirit and scope of the following claims.

What is claimed is:

1. A composition comprising:
a non-aqueous system comprising metal oxide particles, the particles having a first coating and a second coating, wherein the first coating comprises a hydrophobic coating and the second coating comprises an organic dispersant wherein the organic dispersant is present in an amount that renders the coated particles self-dispersible; wherein the hydrophobic coating includes triethoxycaprylylsilane and the organic dispersant includes polyhydroxy stearic acid.

2. The composition of claim 1, wherein the non-aqeuous system is a powder and the first coating is applied to the surface of the metal oxide.

3. The composition of claim 1 wherein the metal oxide particles are micronized or pigmentary grade particles.

4. The composition of claim 3 wherein the metal oxide particles are selected from the group consisting of titanium dioxide, zinc oxide, aluminum oxide, iron oxide, zirconium oxide, chromium oxide, cerium oxide, composites of a metal oxide and composites of a metal oxide and an inorganic salt.

5. The composition of claim 1 wherein the coated substrate is self-dispersible in an organic medium.

6. The composition of claim 1 further comprising an inorganic coating.

7. The composition of claim 6 wherein the inorganic coating is between the substrate and the coating that includes the organic dispersant.

8. The composition of claim 7 wherein the inorganic coating includes an oxide selected from the group consisting of oxides of aluminum, zirconium, silicon, and mixtures thereof.

9. The composition of claim 1 wherein the hydrophobic coating is between the substrate and the coating that includes the organic dispersant.

10. The composition of claim 9 further comprising an inorganic coating selected from the group consisting of oxides of aluminum, zirconium, silicon, and mixtures thereof between the substrate and the hydrophobic coating.

11. The composition of claim 1 further comprising a dispersing medium with the coated substrate dispersed therein.

12. The composition of claim 11 wherein the dispersing medium is selected from an ester, an oil, a hydrocarbon, an alkyl modified silicone fluid, and combinations thereof.

13. The composition of claim 1 wherein the coated substrate is included in a cosmetic composition.

14. The composition of claim 13 wherein the cosmetic composition is a sunscreen.

15. The composition of claim 13 further comprising a biocompatible excipient.

16. The composition of claim 11 wherein the dispersed coated substrate is included in a cosmetic composition.

17. The composition of claim 16 wherein the cosmetic composition is a sunscreen.

18. The composition of claim 16 further comprising a biocompatible excipient.

19. A process comprising:
   providing a particulate metal oxide selected from the group consisting of titanium dioxide, zinc oxide, aluminum oxide, iron oxide, zirconium oxide, chromium oxide, cerium oxide, composites of a metal oxide and composites of a metal oxide and an inorganic salt; wherein the particulate metal oxide is optionally a micronized particulate or a pigmentary grade particulate;
   applying a hydrophobic coating including triethoxycaprylylsilane as a first layer to the surface of the particulate metal oxide to form hydrophobic coated particles,
   applying an outer coating comprising an organic dispersant on the hydrophobic coated particles wherein the dispersant is polyhydroxy stearic acid;
   optionally drying the coated particulate metal oxide; and
   optionally milling the dry coated particulate metal oxide;
   wherein the process renders the coated particulate metal oxide self-dispersible.

20. A coated particulate metal oxide prepared in accordance with the process of claim 19.

21. A cosmetic composition comprising a coated particulate metal oxide prepared in accordance with the process of claim 19.

22. A composition comprising:
   a non-aqueous system comprising coated metal oxide particles, said metal oxide particles being directly coated with a hybrid coating comprising
   a) a first coating comprising a hydrophobic coating including triethoxycaprylylsilane
   b) a second coating comprising an organic dispersant, wherein the organic dispersant is polyhydroxy stearic acid, wherein the organic dispersant is present in an amount that renders the coated particles self-dispersible, wherein the first coating is applied to the surface of the metal oxide directly coating the metal oxide particle and the second coating is the outermost layer of the coated metal particles, wherein the non-aqeuous system is a powder.

* * * * *